US00PP32853P2

(12) United States Plant Patent
Infante Espineira

(10) Patent No.: US PP32,853 P2
(45) Date of Patent: Mar. 2, 2021

(54) NECTARINE TREE NAMED 'ANDES NEC-5'

(50) Latin Name: *Prunus persica*
Varietal Denomination: Andes Nec-5

(71) Applicant: VIVEROS ASOCIADOS CHILE LIMITADA, Santiago (CL)

(72) Inventor: Rodrigo Arturo Infante Espineira, Santiago (CL)

(73) Assignees: VIVEROS ASOCIADOS CHILE LIMITADA, Santiago (CL); UNIVERSIDAD DE CHILE, Santiago (CL)

( * ) Notice: Subject to any disclaimer, the term of this patent is extended or adjusted under 35 U.S.C. 154(b) by 0 days.

(21) Appl. No.: 16/602,590

(22) Filed: Nov. 5, 2019

(51) Int. Cl.
*A01H 5/08* (2018.01)
*A01H 6/74* (2018.01)

(52) U.S. Cl.
USPC ..... Plt./188
CPC ..... *A01H 6/7454* (2018.05)

(58) Field of Classification Search
USPC ..... Plt./188
CPC ..... A01H 6/7454; A01H 5/08
See application file for complete search history.

*Primary Examiner* — Keith O. Robinson
(74) *Attorney, Agent, or Firm* — Greer, Burns & Crain, Ltd.

(57) ABSTRACT

A new and distinct variety of nectarine tree named 'Andes Nec-5' with high vigor, which produces a nectarine with a slow pulp softening rate during the last two weeks before a commercial harvest, the nectarine has a high postharvest life potential, the nectarine is round, symmetrical, it is white in flesh color and most of the nectarine surface is covered by 90 to 100% red blush, and the nectarine has a balanced acid/sweet flavor.

7 Drawing Sheets

Latin name: *Prunus persica* (Nectarine).
Variety denomination: ANDES NEC-5.

BACKGROUND

This new cultivar resulted from controlled hybridization between nectarine 'Andesnectres' (U.S. Plant Pat. No. 25,893), (♀) and nectarine '18-R-47' (not patented) (♂) performed in 2009 at Maipú, Metropolitan Region, Chile (latitude −33° 78'S, longitude −70° 64'S, altitude 210 m above level). This tree was first asexually propagated in July of 2012 and tested on a block of 10 cloned trees in the same experimental station at Maipú and in El Tambo, VI region of Chile.

SUMMARY

The new variety 'Andes Nec-5' differs from its female progenitor 'Andesnectres' (U.S. Plant Pat. No. 25,893), because 'Andes Nec-5' reaches higher content of soluble solids, reaching up to 17% whereas 'Andesnectres' (U.S. Plant Pat. No. 25,893), seldom reaches more than 14%. The male parent, '18-R-47' (not patented) is a white fleshed nectarine that in postharvest lasts no more than 14-21 days in good conditions, whereas the female parent 'Andesnectres' (U.S. Plant Pat. No. 25,893), a yellow fleshed variety, can maintain quality after 40 days in cold storage. In comparison to its male progenitor, the selection '18-R-47' (not patented) is less productive than 'Andes Nec-5', it has high acidity and yellow flesh, whereas 'Andes Nec-5' is a balanced sweet/acid cultivar, reaching ratios around 12.

Distinctive characteristics of 'Andes Nec-5' include the following. Semi upright plant growth with high vigor. The fruit is round, symmetrical, and solid 90 to 100% red blush. Harvest period 15-20 days before 'August Red' (U.S. Plant Pat. No. 6,363).

This cultivar main feature is a slow pulp softening rate during the last two weeks before the commercial harvest. This feature enables delaying harvesting, pursuing an increase of the fruit size and soluble solids content without affecting their postharvest life potential. Secondly, 'Andes Nec-5' has a high postharvest life potential, which can reach up to 40 days at 0° C. while maintaining its initial sensory quality. From a sensory point of view this is a variety of balanced sweetness/acidity ratio and in general an average overall sensory quality. The variety 'Andes Nec-5' is not susceptible to "chilling injury" and therefore, can be used for exporting to distant markets.

BRIEF DESCRIPTION OF THE DRAWINGS

The drawings of the nectarine of the present variety are color photographs.

DETAILED BOTANICAL DESCRIPTION—CHARACTERIZATION OF 'ANDES NEC-5' NECTARINE

Figure 1:
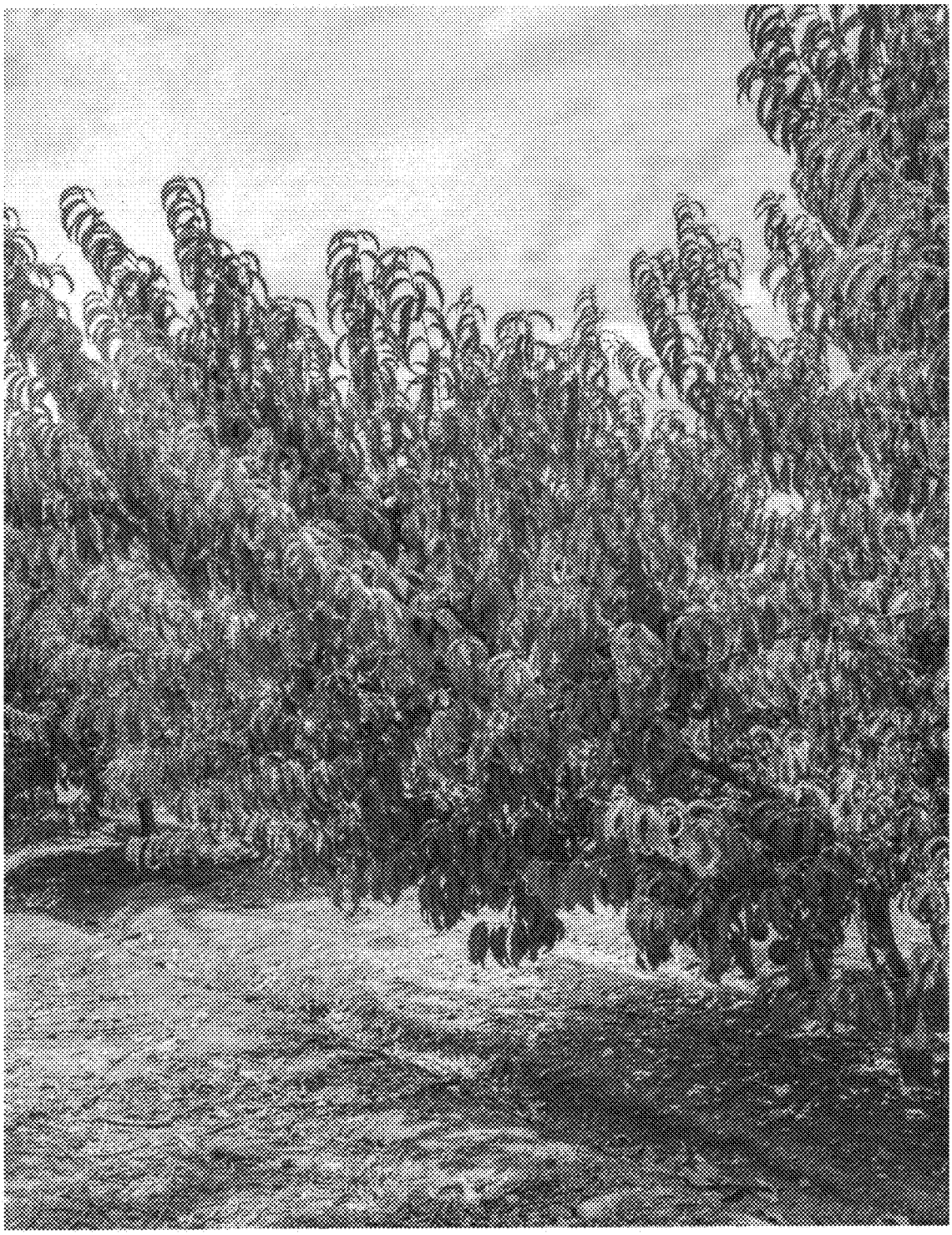
FIG. 1 shows a nectarine tree named 'Andes Nec-5'.
Figure 2:
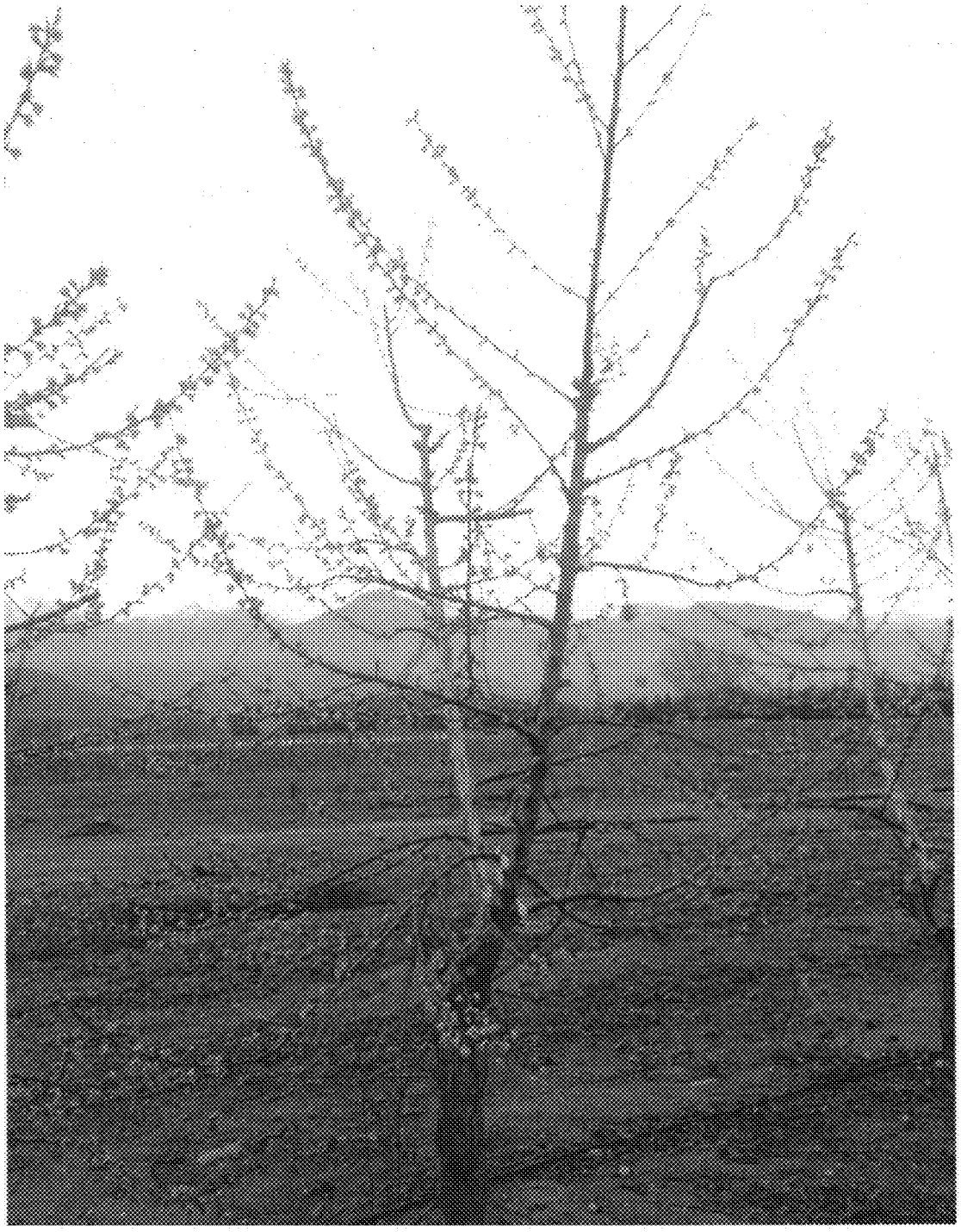
FIG. 2 shows a nectarine tree named 'Andes Nec-5' in bloom.
Figure 3:
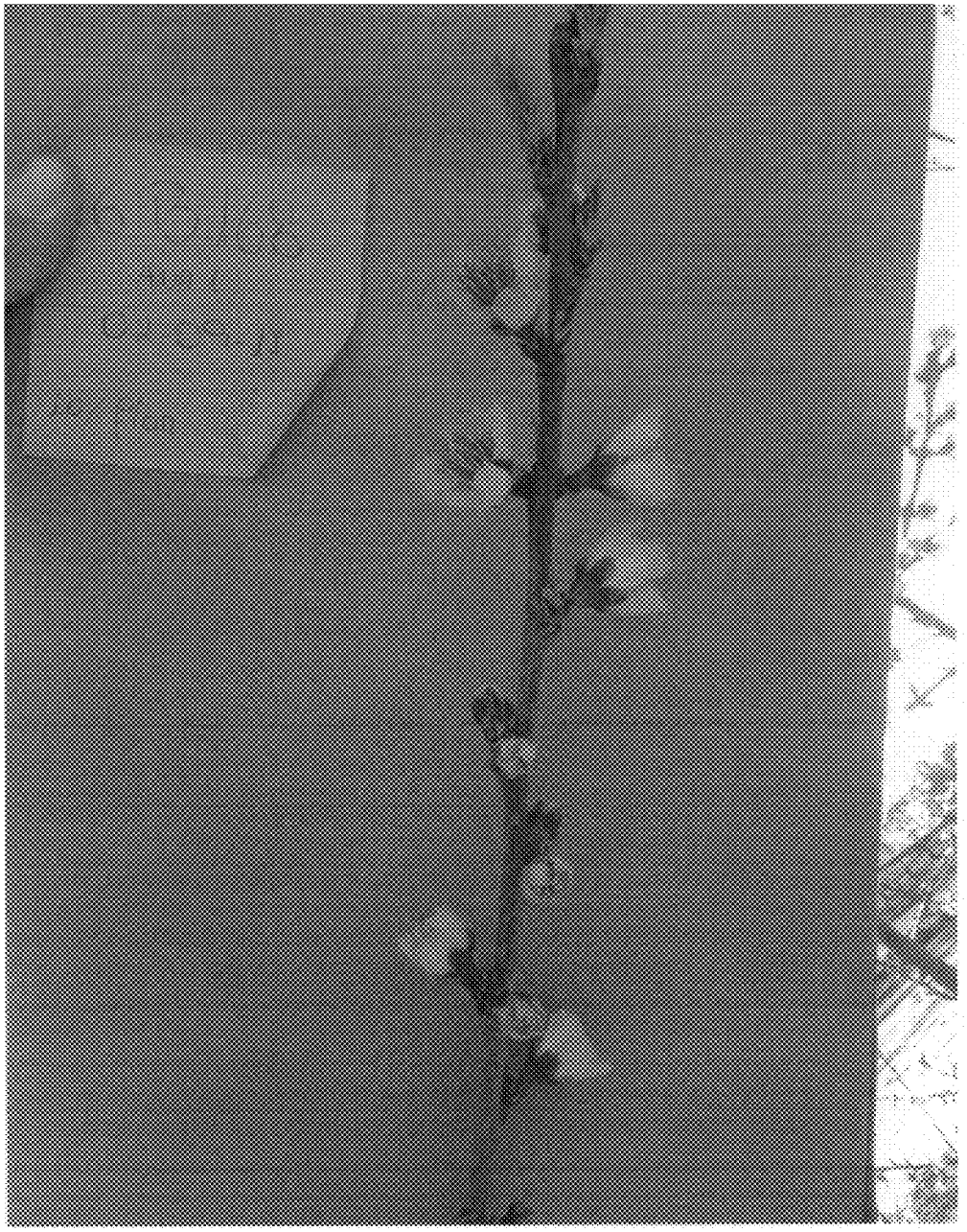
FIG. 3 shows typical specimens of a flower.
Figure 4:
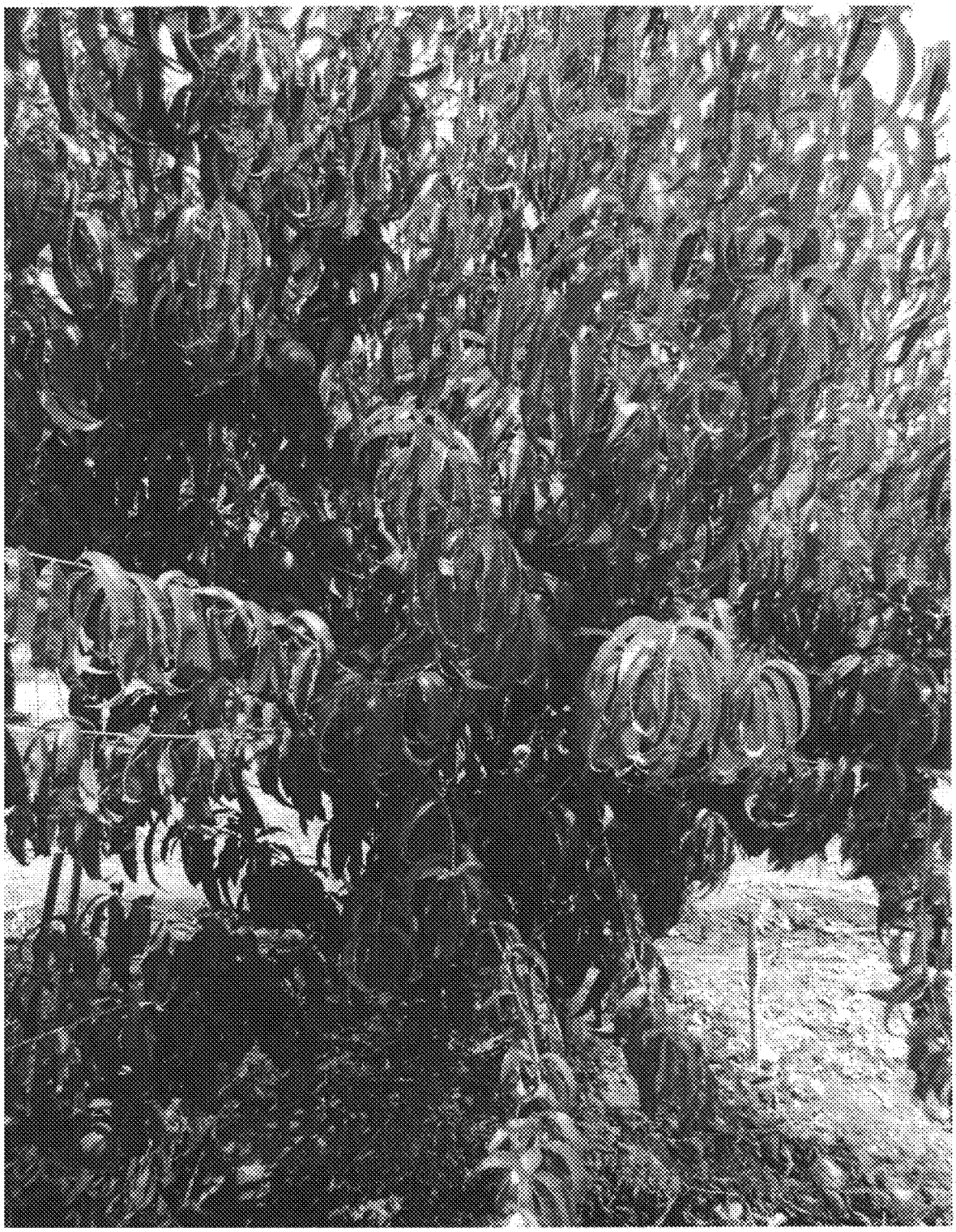
FIG. 4 shows typical specimens of fruit and leaves on a nectarine tree named 'Andes Nec-5'.
Figure 5:
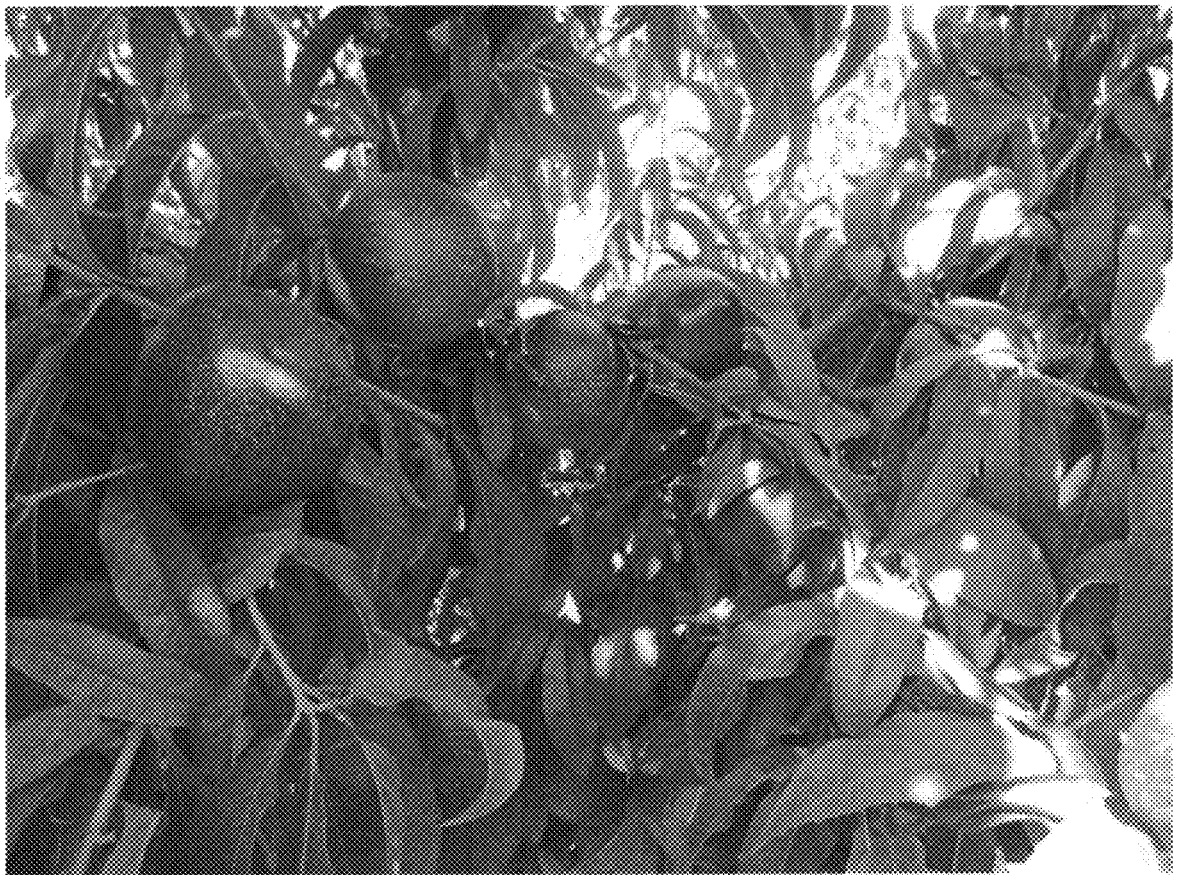
FIG. 5 shows an enlarged view of the fruit and leaves of the tree of FIG. 4.
Figure 6:
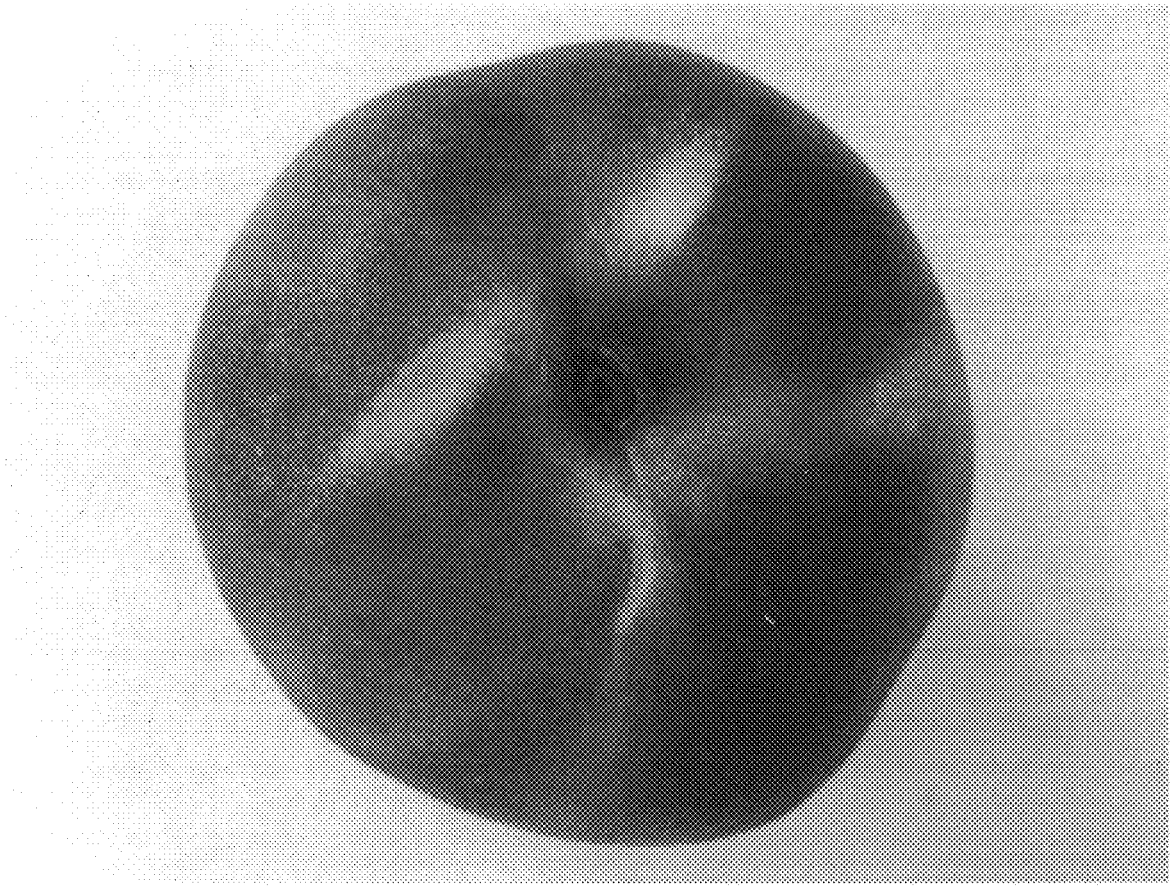
FIG. 6 is a photograph of the fruit.
Figure 7:
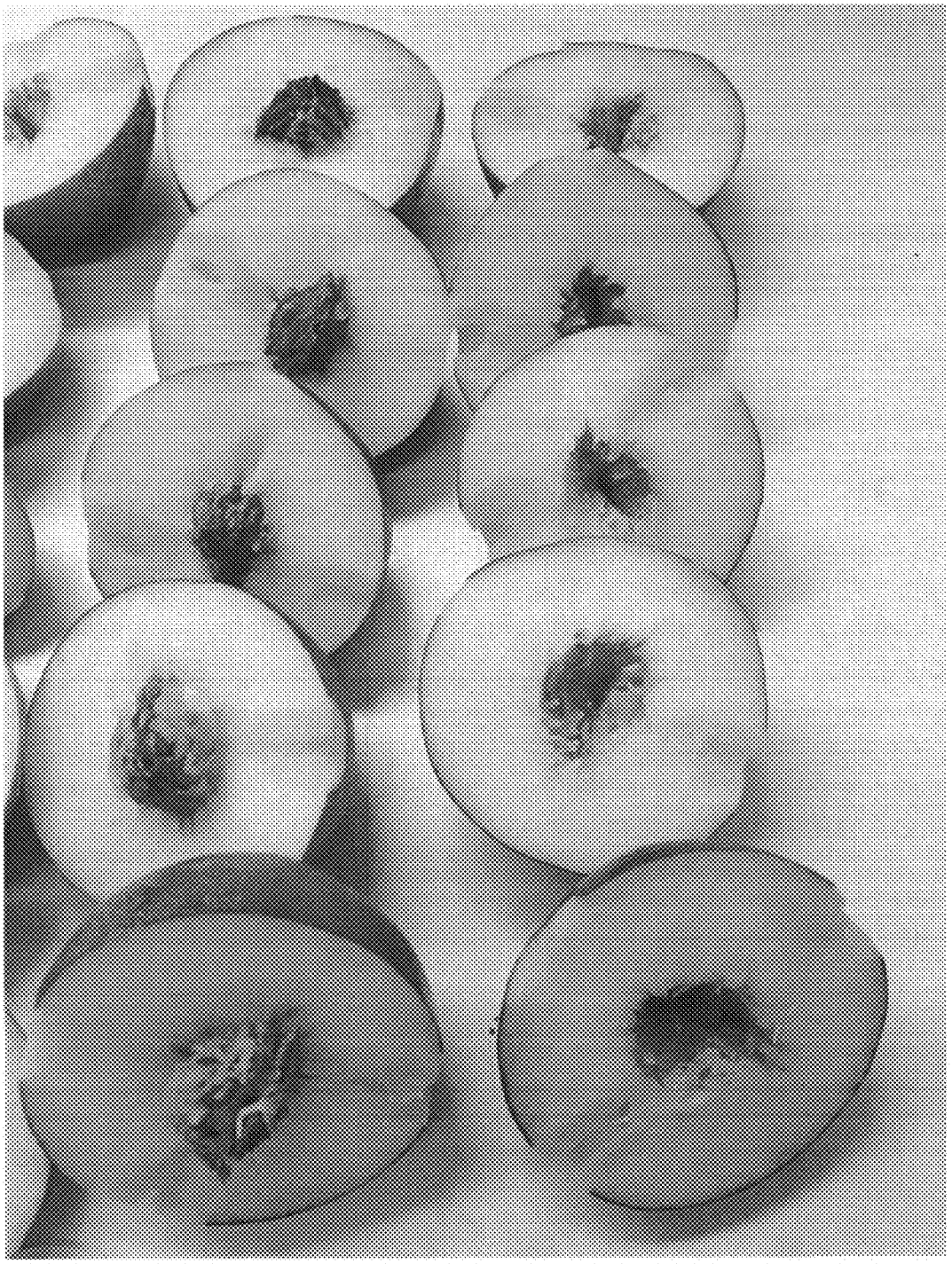
FIG. 7 is a photograph of the fruit flesh and stone.

Color descriptions below are based on evaluations with a Minolta CR-400 colorimeter al CIE D65/0° illumination/ viewer conditions. The color parameters correspond to the uniform color space CIELAB, derived from McGuire (1992). Two color coordinates, a* and b*, as well as a psychometric index of lightness, L*, are defined. The L* is a measurement of luminosity, i.e., the equivalence of each color on the gray scale, ranging from 0 (black) to 100 (White). The a* takes positive values (0 to +60) for reddish colors and negative values (0 to −60) for the greenish ones, whereas the b* takes positive values (0 to +60) for yellowish colors and negative values (0 to −60) for the bluish ones. This is much more precise and repeatable analysis of color than obtained by using color charts. Where a reasonably close match could be discerned, The Munsell Color Chart is also referenced.

Tree:

1. *Size*.—Large, similar to 'Redhaven' (not patented). A 7 year old tree is 4.0-4.5 m high shaped as an open vase, 2.5-3.0 of diameter.
2. *Vigor*.—High, similar to 'Redhaven' (not patented). Shoots reach 25 to 60 cm in length on regular spring/summer growing period.
3. *Habit*.—Upright, like 'Albertina' (not patented). It is well adapted to open vase training.
4. *Flowering shoot thickness* (*excluding brindilles*).—Medium, similar to 'Redhaven' (not patented). The typical and observed flowering shoot diameter is 0.4-0.6 mm.
5. *Flowering shoot length of internodes*.—Medium, similar to 'Redhaven' (not patented). The typical and observed flowering shoot internode length is 2.4-3.0 cm.
6. *Flowering shoot coloration*.—There is present anthocyanin coloration in the zone exposed to sunlight, reaching a light red color, that in coordinates a*, b* and L* of the CIELab space color (McGuire, 1992) corresponds to 45.9, 11.4, and 10.7, respectively, but in the lower part of the shoot the anthocyanin coloration is weak, similar to 'Springtime' (not patented), reaching a light brown color, that in coordinates a*, b* and L* of the CIELab space color (McGuire, 1992) corresponds to 37.0, 7.3, and 12.4, respectively. (McGuire, R. G. 1992. Reporting of Objective Color Measurements. Hortscience. 27(12): 1254-1255).
7. *Flowering shoot density of flower buds*.—Medium, similar to 'Michelini' (not patented), reaching in an average year 25-30 flowers/100 cm long shoot.
8. *Flowering shoot*.—General distribution of flower buds: In groups of two or more, similar to 'Redhaven' (not patented). — 9. The trunk of a 7-year old tree, grafted on Nemaguard (not patented) rootstock, shows a 14-16 cm diameter, measured on 50 cm above the ground, the bark texture is smooth with few lenticels, and the bark color is dark brown, that in coordinates a*, b* and L* of the CIELab space color (McGuire, 1992) corresponds to 44.5, 3.5, and 9.3, respectively. — 10. The primary branches diameter reaches 8-10 cm in a 7-year old tree, and the color is light brown, that in coordinates a*, b* and L* of the CIELab space color (McGuire, 1992) corresponds to 48.2, —2.2, and 23.0, respectively.
11. *Vegetative buds shape and color*.—Acuminate, 4.8-7.5 mm length, color brown that in coordinates a*, b* and L* of the CIELab space color (McGuire, 1992) corresponds to 98.9, −6.0, and 28.3, respectively.

Flower:

12. *Type*.—Campanulate or not showy, similar to 'Springtime' (not patented), reaching a whole diameter of 2.2 to 2.5 cm, and ovary is settled 0.4 to 0.5 cm below the calyx.
13. *Calyx color of inner side* (*opened flower, before falling of petals*).—Pale yellow, similar to 'Robin' (not patented), the color is classified as in coordinates a*, b* and L* of the CIELab space color (McGuire, 1992) corresponds to 58.5, 12.0, and 25.1, respectively.
14. *Corolla predominant color* (*inner side*).—Dark pink, similar to 'Vivian' (not patented), classified in coordinates a*, b* and L* of the CIELab space color (McGuire, 1992) corresponds to 86.6, −1.8, and 10.1, respectively.
15. *Petal shape*.—Medium elliptic, similar to 'Bradgust' (not patented).
16. *Petal size*.—Medium, similar to 'Robin' (not patented), 0.8 to 1.3 cm diameter.
17. *Petals number*.—Five, similar to 'Redhaven' (not patented).
18. *Stamens position compared to petals*.—Above 0.5 to 1.0 mm, similar to 'Redhaven' (not patented).
19. *Stamen number and length*.—There are 30-40 stamens per flower in average 0.8 cm, of white-cream color, in coordinates a*, b* and L* of the CIELab space color (McGuire, 1992) corresponds to 92.0, −3.9, and 9.8, respectively.
20. *Stigma position compared to anthers*.—Above, similar to 'Fuzalode' (not patented).
21. *Pistil*.—There is normally 1 per flower, 12 mm length and white cream color according to in coordinates a*, b* and L* of the CIELab space color (McGuire, 1992) corresponds to 61.7, 3.8, and 10.2, respectively.
22. *Anthers pollen*.—present and abundant, similar to 'Redhaven' (not patented), in number 30 to 40, and the characteristic color is classified in coordinates a*, b* and L* of the CIELab space color (McGuire, 1992) corresponds to 85.5, 4.1, and 42.5, respectively.
23. *Ovary shape*.—Pubescence is absent, similar to 'Fuzalode' (not patented), green color classified in coordinates a*, b* and L* of the CIELab space color (McGuire, 1992) corresponds to 36.0, −88.0, and −16.7, respectively.

Leaf:

24. *Leaf blade length*.—Medium, reaching 12-15 cm long.
25. *Leaf blade width*.—Medium, reaching 4.5-5.5 cm width.
26. *Leaf blade*.—Ratio length/width: Medium, similar to 'Early Sungrand' (not patented), reaching a ratio of 3.5.
27. *Leaf blade shape in cross section*.—Flat, similar to 'Mayred' (not patented).
28. *Leaf blade recurvature of apex*.—Absent, similar to 'Merril Sundance' (not patented).
29. *Leaf blade angle at base*.—Acute, less than 90°, similar to 'Springtime' (not patented).

30. *Leaf blade angle at apex*.—Medium to acute, similar to 'Earlyred' (not patented).
31. *Leaf blade color*.—Green, similar to 'Robin' (not patented), classified in coordinates a*, b* and L* of the CIELab space color (McGuire, 1992) corresponds to 37.0, −8.9, and −16.8, respectively on the upper surface and in coordinates a*, b* and L* of the CIELab space color (McGuire, 1992) corresponds to 58.0, −5.8, and −14.0, respectively, in the lower surface.
32. *Petiole length*.—Medium, similar to 'Genadix-7' (not patented), reaching 2-3 cm.
33. *Petiole*.—Two to four nectaries present, similar to 'Redhaven' (not patented).
34. *Petiole shape of nectaries*.—Reniform, similar to 'Redhaven' (not patented).
35. *Petiole predominant number of nectaries*.—More than two, similar to 'Everts' (not patented).

Fruit:

36. *Fruit size*.—Large, similar to 'Loring', ranging between 190 to 210 g.
37. *Fruit shape* (*in ventral view*).—Circular, similar to 'Redwing' (not patented). The observed fruit length parallel to the suture is 5.7 to 6.8 cm and width perpendicular to the suture is 5.9 to 6.9 cm.
38. *Fruit shape of pistil end*.—Flat, similar to 'Redhaven' (not patented).
39. *Fruit symmetry* (*viewed from pistil end*).—Symmetric, similar to 'Redhaven' (not patented).
40. *Fruit prominence of suture*.—Weak, similar to 'Redhaven' (not patented).
41. *Fruit depth of stalk cavity*.—Shallow, similar to 'Robin' (not patented), ranging between 5-6 mm.
42. *Fruit width of stalk cavity*.—Narrow, similar to 'Redhaven' (not patented). 2.0-2.4 cm.
43. *Fruit ground color*.—Greenish yellow, classified in coordinates a*, b* and L* of the CIELab space color (McGuire, 1992) corresponds to 61.0, 6.1, and 32.1, respectively, similar to 'Veteran' (not patented) when is mature.
44. *Fruit over color*.—Present.
45. *Fruit*.—Hue of over color: 26.42. medium Red, classified as CIELAB, similar to 'Red Diamond' (not patented).
46. *Fruit pattern of over color*.—Solid flush, similar to 'Flavorcrest' (not patented).
47. *Fruit extent of over color*.—Large, reaching 90-100%.
48. *Fruit pubescence*.—Absent.
49. *Fruit thickness of skin*.—Medium, similar to 'Madame Girerd' (not patented).
50. *Fruit adherence of skin to flesh*.—Strong, similar 'Babygold 5' (not patented).
51. *Fruit firmness of pulp*.—Firm.
52. *Fruit ground color of flesh*.—White, classified in coordinates L, Hue and Chroma of the CIELab space color (McGuire, 1992) corresponds to 79.1, 64.2 and 17.8, respectively.
53. *Fruit anthocyanin coloration directly under skin*.—Weakly expressed.
54. *Fruit anthocyanin coloration of flesh*.—Absent, similar to 'Robin' (not patented).
55. *Fruit anthocyanin coloration around stone*.—Very weakly expressed, similar to 'Springtime' (not patented).
56. *Fruit texture of the flesh*.—Not fibrous, melting flesh type, similar to 'Redhaven' (not patented).
57. *Fruit sweetness*.—High, reaching 16-18%.
58. *Fruit acidity*.—Low, ranging between 0.6 to 1.0% malic acid when fruit is ripe.

Stone:

59. *Stone size compared to fruit*.—Small, ranging between 12 to 17 g.
60. *Stone shape* (*in lateral view*).—Elliptic, similar to 'Loring'. The length is 3.1 cm and width 1.8 cm.
61. *Stone intensity of brown color*.—Medium, classified as in coordinates a*, b* and L* of the CIELab space color (McGuire, 1992) corresponds to 26.5, 15.4, and 7.1, respectively.
62. *Stone relief of surface*.—Predominantly grooves.
63. *Stone grooves*.—Similar to 'Madame Girard' (not patented).
64. *Stone tendency of splitting* (*at peak harvest*).—Absent.
65. *Stone adherence to flesh*.—Present, similar to 'Sweet Gold' (not patented).
66. *Stone degree of adherence to flesh*.—Medium, similar to 'Springcrest' (not patented).

Phenology:

67. *Time of leaf bud burst*.—Early, similar to 'Springtime' (not patented). On Southern Hemisphere is between 10th to 25th September.
68. *Time of beginning of flowering*.—Medium, similar to 'Redhaven' (not patented). On Southern Hemisphere is between 5th to 10th August.
69. *Duration of flowering*.—Short, 5-7 days.
70. *Time of maturity for consumption*.—Medium, similar to 'Fairhaven' (not patented). On Southern Hemisphere is between 10th to 15th January.
71. *Tendency to preharvest*.—Absent.
72. *Pest/disease resistance/susceptibility*.—This genotype is not genetically resistant to any common pest and disease of peach, as Mildew (e.g. *Erysiphe* spp., or *Sphaerotheca* spp), leaf curl (genus *Taphrina*, exemplary species *T. deformans*), bacterial canker (genus *Pseudomonas*, exemplary species *P. syringae*), aphids (genus *Aphis*), thrips (genus *Thysanoptera*) or, Oriental moth (genus *Grapholita*, exemplary species *G. molesta*).
73. Fruit characterization is in table 1.

TABLE 1

Fruit characterization of nectarine 'Andes Nec-5'

| SEASON | Harvest Date | Blush % | Equatorial Diameter (mm) | Shoulders | Firmness (Lb) Suture | Tip | Soluble solids (°Brix) |
|---|---|---|---|---|---|---|---|
| 2016-2017 | 1/4 | 95 | 12.9 | 8.8 | 9.6 | 15.1 | 17.0 |
| 2017-2018 | 1/12 | 95 | 13.8 | 11.2 | 11.7 | 15.2 | 16.0 |
| 2018-2019 | 1/11 | 100 | 13.1 | 9.0 | 9.6 | 11.7 | 18.0 |

GENERAL TECHNICAL NOTES

Very good outward appearance. Excellent color coverage. Fruit round, no tip. High productivity. Excellent flavor. After four years of evaluation, the variety continues to show its outstanding characteristics: very good productivity, good size, good flavor and good external appearance. The variety has a high potential for export to Asian countries because of its white flesh and its exceptional post-harvest life potential.

Having this described and illustrated the new variety of nectarine tree, I claim:

1. A new and distinct variety of nectarine tree with high vigor, substantially as illustrated and described, and which produces a nectarine which differs from its progenitor by a slow pulp softening rate during the last two weeks before a commercial harvest, the nectarine has a high postharvest life potential, the nectarine is round, symmetrical, it is white in flesh color and most of the nectarine surface is covered by 90 to 100% red blush, and the nectarine has a balanced acid/sweet flavor.

* * * * *